(12) United States Patent
Coffin (10) Patent No.: US 6,821,753 B2
(45) Date of Patent: Nov. 23, 2004

(54) REPLICATION INCOMPETENT HERPES VIRUSES FOR USE IN GENE THERAPY

(75) Inventor: Robert Stuart Coffin, London (GB)

(73) Assignee: Biovex Limited, London (GB)

(*) Notice: Subject to any disclaimer, the term of this patent is extended or adjusted under 35 U.S.C. 154(b) by 0 days.

(21) Appl. No.: 10/168,796
(22) PCT Filed: Dec. 22, 2000
(86) PCT No.: PCT/GB00/04981
§ 371 (c)(1), (2), (4) Date: Sep. 18, 2002
(87) PCT Pub. No.: WO01/46449
PCT Pub. Date: Jun. 28, 2001

(65) Prior Publication Data
US 2003/0082142 A1 May 1, 2003

(30) Foreign Application Priority Data
Dec. 22, 1999 (GB) ............................................. 9930418

(51) Int. Cl.$^7$ .......................... C12P 21/06; C12P 21/04; C12Q 1/70; C12Q 1/68; C12N 5/00
(52) U.S. Cl. .............................. 435/69.1; 435/5; 435/6; 435/70.1; 435/69.7; 435/172.1; 435/325
(58) Field of Search ............................. 435/5, 6, 69.1, 435/70.1, 69.7, 172.1, 325

(56) References Cited

FOREIGN PATENT DOCUMENTS

| WO | WO 97/20935 | 6/1997 |
| WO | WO 98/04726 | 2/1998 |
| WO | WO 98/30707 | 7/1998 |
| WO | WO 99/38955 | 8/1999 |
| WO | WO 99/60145 | 11/1999 |

OTHER PUBLICATIONS

Lachmann et al "The Use of Herpes Simplex Virus–Based Vectors for Gene Delivery to The Nervous System", Molecular Medicine Today, pp. 404–411 (XP–000783616) (1997).

(List continued on next page.)

Primary Examiner—Hankyel T. Park
(74) Attorney, Agent, or Firm—Nixon & Vanderhye PC

(57) ABSTRACT

Use of a replication incompetent herpes virus capable of delivering a gene to multiple connected sites within the nervous system, which virus comprises: (a) a mutation which prevents or reduces the expression of at least two immediate early genes; and (b) a heterologous gene operably linked to a promoter active during herpes virus latency; in the manufacture of a medicament for the treatment of a central nervous system disorder, a method of determining whether a gene has an effect on a phenotype associated with a central nervous system disorder and in a method of treatment of a disorder of the central nervous system are described.

36 Claims, 1 Drawing Sheet

OTHER PUBLICATIONS

Samaniego et al. "Persistence and Expression of the Herpes Simplex Virus Genome in the Absence of Immediate–Early Proteins", J. Virol. 72(4):3307–3320 (1998).

Thomas et al. "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate–Early Gene Defects" J. Virol. 73(9):7399–7409 (1999).

Ace et al. "Construction and characterisation of a hepes simplex virus type mutant unable to transinduce immediate early gene expression" J. Virology 63:2260–2269 (1989).

Batterson & Roizman "Characterisation of the herpes simplex virion–associated factor responsible for induction of $\alpha$ genes" J. Virology 46:371–377 (1983).

Bloom et al. "Long term expression of a reporter gene from latent herpes simplex virus in the rat hippocampus" Mol. Brain Res. 31:48–60 (1995).

Carpenter & Stevens "Long–term expression of a foreign gene from a unique position in the latent herpes simplex virus genome" Hum. Gene Therapy 7:1447–1454 (1996).

Coffin & Latchman "Herpes simplex virus–based vectors" In: Genetic Manipulation of the Nervous System, pp. 99–114 Academic Press, London (1996).

Coffin et al. "Gene delivery to the central and peripheral nervous system of mice using HSV1 ICP34.5 deletion mutant vectors" Gene Therapy 3:886–891 (1996).

DeLuca et al. "Isolation and characterisation of deletion mutants of herpes simplex virus type 1 in the gene encoding immediate–early regulatory protein ICP4" J. Virology 56:558–570 (1985).

DeLuca & Schaffer "Activities of herpes simplex virus type 1 (HSV–1) ICP4 genes specifying nonsense peptides" Nucl. Acids Res. 15:4491–4511 (1987).

Dobson et al. "In vivo deletion analysis of the herpes simplex virus type 1 latency–associated transcript promoter" J. Virology 69:2264–2270 (1995).

Fink et al. "Gene transfer to neurons using herpes simplex virus–based vectors" Ann. Rev. Neurosci. 19:265–287 (1996).

Gelman & Silverstein "Dissection of immediate–early gene promoters from herpes simplex virus: Sequences that respond to the virus transcriptional activators" J. Virology 61:3167–3172 (1987).

Goins et al. "A novel latency–active promoter is contained within the herpes simplex virus type 1 $U_L$ flanking repeats" J. Virology 68:2239–2252 (1994).

Goldstein & Weller "Herpes simplex virus type–1–induced ribonucleotide reductase activity is dispensible for virus growth and DNA synthesis: Isolation and characterisation of an ICP6 lacZ insertion mutant" J. Virology 62:196–205 (1988).

Gossen et al. "Transcriptional activation by tetracyclines in mammalian cells" Science 268:1766–1769 (1995).

Gossen & Bujard "Tight control of gene expression in mammalian cells by tetracyline–responsive promoters" Proc. Nat. Acad. Sci. USA 89:5547–5551 (1992).

Ho & Mocarski "$\beta$–galactosidase as a marker in the peripheral and neural tissues of the herpes simplex virus–infected mouse" Virology 167:279–283 (1988).

Howard et al. "High efficiency gene transfer to the central nervous system of rodents and primates using herpes virus vectors lacking functional ICP27 and ICP34.5" Gene Therapy 5:1137–1147 (1998).

Johnson et al. "Cytotoxicity of a replication–defective mutant of herpes simplex virus type 1" J. Virology 66:2952–2965 (1992).

Johnson et al. "Improved cell survival by the reduction of immediate–early gene expression in replication–defective mutants of herpes simplex virus type–1 but not by mutation of the virion host shutoff function" J. Virology 68:6347–6362 (1994).

Krisky et al. "Deletion of multiple immediate–early genes from herpes simplex virus reduces cytotoxicity and permits long–term gene expression in neurons" Gene Therapy 5:1593–1603 (1998).

Lachman & Efstathiou "Utilisation of the herpes simplex virus type 1 latency associated regulatory region to drive stable reporter gene expression in the nervous system" J. Virology 71:3197–3207 (1997).

Lokensgard et al. "Long–term promoter activity during herpes simplex virus latency" J. Virology 68:7148–7158 (1994).

Lokensgard et al. "The latency associated promoter of herpes simplex virus type 1 requires a region downstream of the transcription start site for long–term expression during latency" J. Virology 71:674–6719 (1997).

MacFarlane et al. "Hexamethylene bisacetamide stimulates herpes simplex virus immediate early gene expressions in the absence of trans–induction by Vmw65" J. Gen. Virology 73:285–292 (1992).

Meignier et al. "In vivo behaviour of genetically engineered herpes simplex viruses R7017 and R7020: Construction and evaluation in rodents" J. Infect. Dis. 159:602–614 (1988).

Pellet et al. "Nucleotide sequence and predicted amino acid sequence of a protein encoded in a small herpes simplex virus DNA fragment capable of trans–inducing $\alpha$ genes" Proc. Natl. Acad. Sci. USA 82:5870–5874 (1985).

Post & Roizman "A generalised technique for deletion of specific genes in large genomes: $\alpha$ gene 22 of herpes simplex virus 1 is not essential for growth" Cell 25:227–232 (1981).

Preston & Nicholl "Repression of gene expression upon infection of cells with herpes implex virus type 1 mutants impaired for immediate early protein synthesis" J. Virology 71:7807–7813 (1997).

Rice & Knipe "Genetic evidence for two distinct transactivation functions of the herpes simplex virus and protein ICP27" J. Virology 64:1704–1715 (1990).

Sacks & Schaffer "Deletion mutants in the gene encoding the herpes simplex virus type 1 immediate–early protein ICP0 exhibit impaired growth in cell culture" J. Virology 61:829–839 (1987).

Samaniego et al. "Functional interactions between herpes simplex virus immediate–early proteins during infection: Gene expression as a consequence of ICP27 and different domains of ICP4" J. Virology 69:5705–5715 (1995).

Samaniego et al. "The herpes simplex virus immediate–early protein ICP0 affects transcription from the viral genome and infected cell survival in the absence of ICP4 and ICP27" J. Virology 71:4614–4625 (1997).

Sears et al. Herpes simplex virus 1 mutant deleted in the α22 gene: Growth and gene expression in permissive and restrictive cells and Establishment of Latency in Mice, J. Virol. 55:338–346 (1985).

Smiley & Duncan "Truncation of the C–terminal acidic transcriptional activation domain of herpes simplex virus VP16 produces a phenotype similar to that of the in 1814 linker insertion mutation" J. Virology 71:6191–6193 (1997).

Smith et al. "Evidence that the herpes simplex virus immediate early protein ICP27 acts post–transcriptionally during infection to regulate gene expression" Virology 186:74–86 (1992).

Stow & Stow "Isolation and characterization of a herpes simplex virus type 1 mutant containing a deletion within the gene encoding the immediate early polypeptide Vmw110" J. Gen. Virology. 67:2571–2585 (1986).

Sze & Herman "The herpes simplex virus type 1 ICP6 gene is regulated by a 'leaky' early promoter" Virus Res. 26:141–152 (1992).

Thompson et al. "DNA sequence and RNA transcription through a site of recombination in a non–neurovirulent herpes simplex virus intertypic recombinant" Virus Genes 1:275–286 (1988).

Wagstaff et al. "Gene transfer using a disabled herpes virus vector containing the EMCV IRES allows multiple gene expression in vitro and in vivo" Gene Therapy 5:1566–1570 (1998).

Wu et al. "Prolonged gene expression and cell survival after infection by a herpes simplex virus mutant defective in the immediate early genes encoding ICP4, ICP27 and ICP22" J. Virology 70:6358–6369 (1996).

Figure 1:
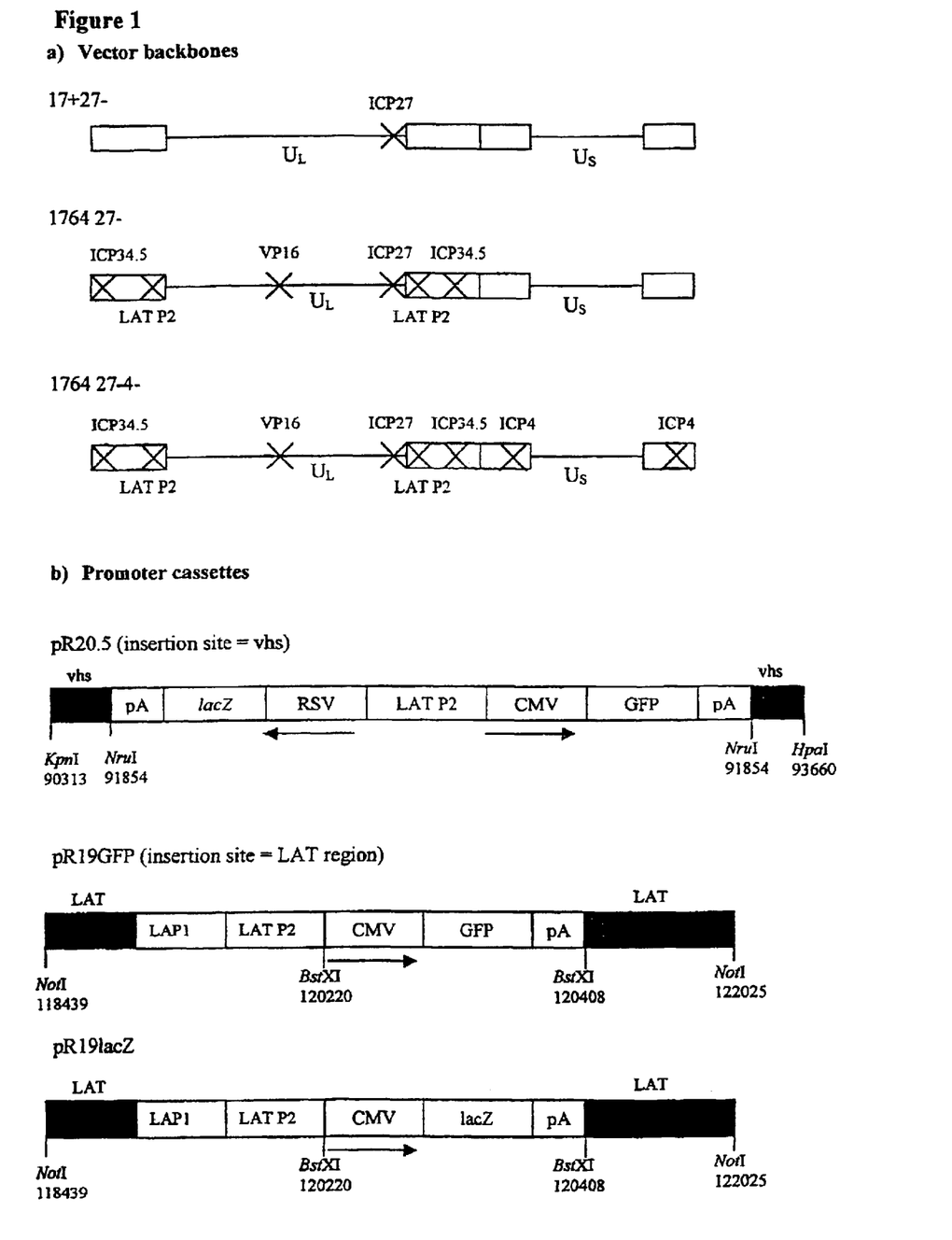

Figure 1
a) Vector backbones

17+27−

1764 27−

1764 27−4− b) Promoter cassettes pR20.5 (insertion site = vhs)

pR19GFP (insertion site = LAT region)

pR19lacZ

REPLICATION INCOMPETENT HERPES VIRUSES FOR USE IN GENE THERAPY

This application is a national phase application of International Patent Appln. No. PCT/GB00/04981 filed Dec. 22, 2000, which designated the United States and was published in English.

FIELD OF THE INVENTION

The present invention relates to replication incompetent herpes simplex viruses capable of efficiently transferring genes to multiple sites within the nervous system. It also relates to the use of such viruses in the study and treatment of diseases and conditions of the nervous system.

BACKGROUND TO THE INVENTION

Herpes simplex viruses (HSV) 1 and 2 have often been suggested as a vector for gene delivery to the nervous system and also other cell types (for reviews see Coffin and Latchman 1995, Fink et al. 1996). As a vector HSV has a number of potential advantages in that it naturally enters latency in neurons, providing the possibility of long term gene expression, does not integrate into the host genome, preventing insertional mutagenesis (for example the activation of oncogenes or inactivation of tumour suppressor genes), can accept very large DNA insertions allowing the delivery of multiple genes, is easy to propagate, and can infect a wide variety of other cell types as well as neurons. HSV also has the unique ability among viruses currently under development as vectors in that it can be efficiently transported along nerves to the cell body (usually in the spine) by retrograde axonal transport following an initial peripheral infection. However, while this property of retrograde axonal transport of HSV vectors has been observed with replication competent vectors in the peripheral nervous system (PNS), it has not previously been exploited in vectors used in the central nervous system (CNS), probably due to limitations in the vectors which have previously been available.

While HSVI is highly prevalent in the human population, in the vast majority of cases giving no obvious signs of disease, for use as a vector the virus must be disabled for safety and so as to minimise toxicity to target cells. Various strategies for disablement have been reported including the removal of genes which are unnecessary for growth in vitro but necessary for pathogenesis in vivo. Such genes include those encoding thymidine kinase (TK; Ho and Mokarski 1988), ribonucleotide reductase (Goldstein and Weller 1988) and ICP34.5 (Coffin et al. 1995). However for minimal toxicity it has become apparent that expression of the regulatory immediate early genes ICPO, ICP4, ICP22 and ICP27, which are themselves cytotoxic, must be minimised (Johnson et al. 1994, Johnson et al. 1992, Wu et al. 1996, Samaniego et al. 1998, Krisky et al. 1998). Such reductions in IE gene expression minimise transcription from the vast majority of the 80 or so other genes in the HSV genome. Removal of ICP4 or ICP27 completely prevents virus growth and so such deletions must be complemented in the cells used for virus propagation (e.g. Deluca et al. 1985). Deletion of ICP22 and/or ICPO, while these genes are not absolutely essential for virus growth (Sacks and Shaffer 1987, Stow and Stow 1986, Post and Roizman 1981, Sears et al. 1985), reduces virus titre. Thus for the growth of HSV mutants with multiple IE gene deficiencies, cell lines must be produced which effectively complement deletions from the virus, and for effective growth of viruses with deletions in ICP4, ICP27, ICP22 and ICPO, all these deficiencies would optimally need to be complemented. However as the IE proteins are highly cytotoxic (Johnson et al. 1994), IE gene expression in cell lines must be tightly regulated. This is usually achieved by the use of the homologous IE gene promoters which are relatively inactive in the absence of virus infection (e.g. E5 cells [ICP4], B130/2 cells [ICP27], E26 cells [ICP4+ICP27], F06 cells [ICP4+ICP27+ICPO]; Deluca and Schaffer 1987, Howard et al. 1998, Samaniego et al. 1995, Samaniego et al. 1997). This reduces the problem of IE protein cytotoxicity but still leaves an inherent problem in the generation of cells which are highly effective at complementing multiple IE gene deficiencies.

A second strategy to reduce IE gene expression, rather than deletion of the IE genes themselves, is to include mutations in the gene encoding vmw65. vmw65 is a virion protein which transactivates IE promoters after virus infection (Batterson and Roizman 1983, Pellet et al. 1985), and while an essential structural protein, specific mutations abolish the trans-activating capability of the protein without affecting the structural integrity of the virus (Ace et al. 1989, Smiley and Duncan 1997). These mutations vastly reduce IE gene expression although at high multiplicity or with the inclusion of hexamethylene bisacetamide (HMBA) in the media still allow efficient virus growth in culture (McFarlane et al. 1992).

Thus, for the construction of vector viruses the approach could also be taken of combining mutations in vmw65, which should reduce expression of all the IE genes, with deletion of ICP27 and/or ICP4, the two essential IE genes, giving viruses as above in which overall IE gene expression is minimised. This is the approach we have taken to generate non-toxic HSV vectors in which IE gene expression has been minimised but which can still be grown in culture using cell lines containing the genes encoding ICP27, ICP4 and the equine herpes virus (EHV) homologue of vmw65 (encoded by EHV gene 12; Thomas et al. 1999).

The development of HSV vectors has also required a second problem to be overcome before they can be used to take advantage of the natural lifecycle of the virus in which a latent state is maintained in neurons. This problem results from the finding that in most cases promoters driving genes inserted into an HSV vector genome are rapidly transcriptionally inactivated as the virus enters latency, including the promoter which usually drives the expression of the only HSV transcripts present during latency, the latency associated transcripts (LATs). To solve this problem, a number of approaches have been taken:

First, it was found that a Moloney murine leukaemia virus (MMLV) promoter linked to a fragment of the LAT promoter ('LAP 1'; Goins et al. 1994) and inserted into the gene encoding glycoprotein C (gC) was able to drive expression during latency, although neither LAPI or the MMLV promoter alone, or a number of other promoters linked to LAPI or alone allowed this to occur (Lokensgard et al. 1994). MMLV alone inserted in ICP4 (Dobson et al. 1990, Bloom et al. 1995) or in LAPI (Carpenter and Stevens 1996) however was active, which may be speculated to be due to the proximity of these regions to the endogenous LATs rather than when distant to the LAT region (in gC) as before. In other approaches it was found that LAP2 alone could give expression during latency when inserted in gC (Goins et al. 1994), but this expression was very weak, and that LAP2 linked to LAPI, like MMLV linked to LAPI, could also maintain latent gene expression when inserted in gC (Lokensgard 1997). Finally it was found that insertion of an internal ribosome entry site (IRES) into the 2 Kb LAT allowed expression of a downstream marker gene (with poly A site) during latency (Lachmann and Efstathiou 1997). However while the above approaches have demonstrated latent gene expression in the PNS, as yet latent gene expression in the brain has only been demonstrated in a very small number of transduced cells (Dobson et al. 1990, Bloom et al. 1995, Carpenter and Stevens 1996) and effective replication defective disabled HSV vectors for the long term gene transfer to the brain have not previously been available.

We have taken an alternative approach to the development of promoters allowing latent gene expression from within the context of an HSV vector where we have found that elements of the LAT region can be used to confer a long term activity onto promoters which are not usually active during latency by placing them downstream of a region designated LAT P2 (promoters inserted after HSVI nt 120,219; Genbank file HEICG: W098/30707). For example a cytomegalovirus (CMV) IE promoter and some other promoters including a minimal neuron specific enolase (NSE) promoter and the Moloney murine leukaemia virus (MMLV) LTR promoter placed in such a context remain active during latency, even though when placed elsewhere latent gene expression with such promoters is generally very inefficient.

SUMMARY OF THE INVENTION

As discussed above, HSV has the unique property among viruses currently under development as vectors in that it can be efficiently transported along nerves before entering latency in neuronal cell bodies. However it has not previously been found that this property can be exploited for gene delivery in the CNS using disabled herpes vectors, as replication incompetent, herpes vectors so far used in the CNS have not demonstrated such properties as gene delivery has always been limited to the site of inoculation. The present inventors have identified disabled, replication incompetent herpes vectors which allow gene delivery to multiple regions within the brain following vector inoculation to only a single brain region. This results from highly efficient retrograde transport of the vectors to cell bodies at connected sites. The inventors have also identified the properties of the vectors which allows this to occur. Replication incompetent herpes vectors allowing such gene delivery to occur combine the use of highly disabled replication incompetent vector backbones with promoter systems which are capable of directing gene expression in the long term. The surprising finding was made that vectors which were either less disabled than those provided by the invention (ie which potentially showed greater toxicity), or which contain promoter cassettes which are incapable of directing latent gene expression, do not allow such widespread gene delivery to occur, even in the short term. Replication incompetent herpes virus vectors as identified by the present inventors may be used in methods of studying or treating disorders of the central nervous system. In particular such vectors may be used in methods of target validation, for example, by screening genes to identify genes important in a central nervous system disorder.

Accordingly, the present invention provides:

a use of a replication incompetent herpes virus comprising:
(a) a mutation which prevents or reduces the expression of at least two immediate early genes; and
(b) a heterologous gene operably linked to a promoter active during herpes virus latency
in the manufacture of a medicament for use in treating or preventing a central nervous system disorder;

a method of determining whether a gene has an effect on a phenotype associated with a central nervous system disorder or on a cell of the central nervous system which is relevant to a central nervous system disorder, which method comprises:
(i) inoculating into a cell of the central nervous system in vivo or in vitro with a replication incompetent herpes virus comprising:
(a) a mutation which prevents or reduces the expression of at least two immediate early genes; and
(b) a heterologous gene operably linked to a promoter active during herpes virus latency; and
(ii) monitoring a phenotype of said disorder or an effect of expression of said gene on said cell to determine thereby whether said gene has an effect on said cell or said phenotype;

a method of screening genes implicated in a central nervous system disorder to identify a target for gene therapy or for small molecule modulators, which method comprises a method of determining whether a gene influences a phenotype associated with a central nervous system disorder according to the invention;

a method of treating a subject suffering from a disorder of the central nervous system, which method comprises administering a therapeutically effective amount of a replication incompetent herpes virus comprising:
(a) a mutation which prevents or reduces the expression of at least two immediate early genes; and
(b) a heterologous gene operably linked to a promoter active during herpes virus latency
to a subject suffering from a disorder of central nervous system;

The present invention is exemplified using vectors in which immediate early gene expression has been minimised by deletion of ICP27 and ICP4 and with a mutation minimising the transactivating capabilities of vmw65, although other similarly non-toxic vector backbones may be used. The invention is also exemplified using vectors in which the LAT region has been used to confer long term activity onto a promoter not usually active in the long term, although other promoter systems active during latency might be used, including those discussed above (Lokensgard et al. 1994, 1997, Goins et al. 1994, Lachmann and Efstathiou 1997).

The term heterologous gene is intended to embrace any gene not found in the viral genome. The heterologous gene may be any allelic variant of a wild-type gene, or it may be a mutant gene. Heterologous genes are preferably operably linked to a control sequence permitting expression of said heterologous gene in a cell of the nervous system. Viruses of the invention may thus be used to deliver a heterologous gene/genes to cells of the nervous system where it will be expressed in multiple regions following inoculation to anatomically connected site(s).

DETAILED DESCRIPTION OF THE INVENTION

Viruses

The present invention provides a method for identifying a gene that may be used as a target for therapeutic intervention in the treatment or prevention of a peripheral nervous system disorder. Such genes are identified by expressing a test gene in a cell of the central nervous system, preferably a neuronal cell, using a replication incompetent herpes virus vector that expresses no or only minimal levels of the essential immediate early genes to deliver the gene to the cell and by determining whether expression of the gene affects a phenotype associated with a central nerve system disorder. A method of determining whether a gene influences a phenotype associated with a central nervous system disorder consists essentially of the following steps:

(i) inoculating the central nervous system in vivo or in vitro with a replication incompetent herpes virus comprising:

(a) a mutation which prevents or reduces the expression of at least two immediate early genes; and (b) a heterologous gene operably linked to a promoter active during herpes virus latency; and (ii) monitoring a phenotype of said disorder to determine thereby whether expression of said gene has an effect on said phenotype.

Typically the herpes virus is capable of delivering the heterologous gene to multiple connected sites within the nervous system such that the heterologous gene is expressed at one or more site distant from the site of inoculation. Preferably the heterologous gene is expressed at multiple connected sites in the central nervous system including the site where the virus was inoculated. Preferably, where the cell is in a neuronal culture the gene is expressed for extended periods such as from 1 month to 1 year, for example for 2, 3, 4, 5, or 6 months.

The present invention provides a method for screening genes to identify a gene which is important in a central nervous system disorder and which may be used as a target for identifying agents for treating the disorder.

The present invention also provides the use of a replication incompetent herpes virus vector that expresses no or only minimal levels of the essential immediate early genes as described herein in the manufacture of a medicament for the treatment of a central nervous system disorder. A method of treating of a subject suffering from a nervous system disorder by administering a therapeutically effective amount of a replication incompetent herpes virus vector as described herein to the central nervous system of a subject in need thereof is also provided by the present invention. The herpes virus vector is typically replication incompetent, does not express significant levels of the immediate early genes ICP0, ICP4, ICP22 and ICP27 and infects at least one site in the CNS that is connected to but distant from the site of inoculation. For example, a virus inoculated into the striatum may be expressed in the substantia nigra.

A virus of the invention is capable of infecting a cell of the nervous system following inoculation, but is incapable of replicating in any cell unless at least one gene which has been rendered non-functional in the virus is also expressed in the cell, i.e. the virus is replication incompetent other than in the cells in which virus stocks are prepared.

By definition such viruses are attenuated such that they are replication incompetent. Viral regions altered for the purposes of such attenuation may be eliminated (completely or partly), made non-functional, or substituted by other sequences, in particular by a heterologous gene sequence. Attenuating mutations resulting in a replication incompetent virus have been described for all neurotrophic herpes viruses so far described. A virus is replication incompetent if it is incapable of replicating in a cell which does not express at least one functional viral gene. Replication incompetent viruses are generally capable of replicating in cell lines which express a functional essential viral gene which compensates for the absence of a functional essential viral gene in the replication incompetent virus. Such cell lines may be used to prepare viral stocks.

Although the present invention has been exemplified using herpes simplex viruses, it will be understood that other neurotrophic viruses of the herpesviridae family may be modified such that they are replication incompetent and can achieve efficient gene delivery to multiple sites within the nervous system following inoculation to a single site. In particular, such viruses may include varicella zoster virus, pseudo-rabies virus or bovine herpes viruses.

When the virus of the invention is a herpes simplex virus, the virus may be derived from, for example, HSVI or HSV2 strains, or derivatives thereof, preferably HSV1. Derivatives include inter-type recombinants containing DNA from HSVI and HSV2 strains. Such inter-type recombinants are described in the art, for example in Thompson et al. 1998 and Meignier et al. 1988. Derivatives preferably have at least 70% sequence homology to either the HSVI or HSV2 genomes, more preferably at least 80%, even more preferably at least 90 or 95%. Derivatives may share sequence homology or identity with a wild type HSV1 or HSV2 genome prior to mutation to produce a virus for use in a method of the invention. Preferably a derivative shares sequence homology or identity with a HSV1 or HSV2 viral strain falling within the scope of the invention.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

For example the UWGCG Package provides the BEST-FIT program which can be used to calculate homology (for example used on its default settings) (Devereux et al. (1984) *Nucleic Acids Research* 12, p387–395). The PILEUP and BLAST algorithms can be used to calculate homology or line up sequences (typically on their default settings), for example as described in Altschul (1993) J. Mol. Evol. 36:290–300; Altschul et al. (1990) J. Mol. Biol. 215:403–10.

Software for performing BLAST analyses is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Viruses of the invention do not express, or express only very low levels of at least two immediate early genes. Very low levels are levels below the detection limit of a western blot using an antibody to a protein product of an immediate early gene. A virus may comprise any suitable mutation which minimises immediate early gene expression. Preferably a virus does not express, or expresses only very low levels of at least three immediate early genes. More preferably a virus does not expresses, or expresses only very low levels of at least four immediate early genes. The immediate early genes which must not be expressed or be expressed at only minimal levels are ICP0, ICP4, ICP22 and ICP27. The two immediate early genes may be ICP27 and ICP4, ICP27 and ICP0, ICP27 and ICP22, ICP4 and ICP0, ICP4 and ICP22 or ICP0 and ICP22.

Viruses may be functionally inactive for individual (e.g. ICP27 or ICP4) or multiple (ICP27 and/or ICP4 and/or ICP22 and/or ICPO and/or ICP47) immediate early genes, or they may additionally contain a mutation in the gene encoding vmw65 reducing/preventing its transcriptional activation capability. Alternatively essential genes may be deleted which are not immediate early genes, either alone, in any combination, or in combination also with the inactivation of an immediate early gene or genes or vmw65. Examples of such viruses include viruses reported by Samaniego et al. 1998, Krisky et al. 1998, or Thomas et al. 1999. Particularly preferred embodiments include viruses in which immediate early gene expression has been prevented or minimised such as those with inactivating mutations in or deletions of the genes encoding ICP4, ICP27, ICPO and ICP22, or alternatively with inactivating mutations in or deletions of ICP27 and/or ICP4 with a mutation in vmw65 reducing or preventing its trans-activating activity.

The terminology used in describing the various HSV genes is as found in Coffin and Latchman, 1996.

Production of Viruses

When the herpes simplex viruses of the invention lack a particular functional essential gene, for example a gene encoding ICP4 or ICP27, the virus of the invention is propagated on a cell line expressing that essential gene. For example, when the virus lacks a functional ICP27 gene, the virus may be propagated on V27 cells (Rice and Knipe, 1990), 2-2 cells (Smith et al., 1992) or B 130/2 cells (Howard et al. 1998). When the virus lacks a functional ICP4 gene the virus may be propagated on a cell line expressing ICP4, for example E5 cells (DeLuca et al., 1985). When the virus lacks a functional ICP4 gene and a functional ICP27 gene the virus is propagated on a cell line expressing both ICP4 and ICP27 (such as E26 cells; Samaniego et al., 1995), and when the virus additionally lacks a functional vmw65 gene the virus may be propagated on a cell line also containing a non-HSV homologue of vmw65 (e.g. from equine herpes virus as in Thomas et al. 1999). Mutations to vmw65 may also be partially compensated for by inclusion of hexamethylene bisacetamide (HMBA) in the media used for virus growth (MacFarlane et al. 1992).

ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27-HSV strains, using methods known to those skilled in the art (for example as described in Rice and Knipe, 1990).

Cell lines which do not allow reversion of an ICP27-mutant HSV strain to a strain with functional ICP27 are produced as described above, ensuring that the vector comprising a functional ICP27 gene does not contain sequences that overlap with (i.e. are homologous to) sequences remaining in the ICP27-mutant virus.

Where HSV strains of the invention comprise inactivating modifications in other essential genes, for example ICP4, complementing cell lines will comprise a functional HSV gene which complements the modified essential gene in the same manner as described for ICP27. For example in the case of HSV strains comprising mutations in both ICP27 and ICP4, a cell line expressing both ICP27 and ICP4 is used such as E26 cells (Samaniego et al., 1995). HSV strains expressing other essential genes can be constructed in a similar manner to that described for ICP27. Here again, if it is ensured there is no sequence overlap between the remaining virus DNA and that inserted into the cell line for virus growth, the possibility of reversion of the virus to a less disabled form during growth will be minimised.

Methods of Mutation

The various viral genes referred to may be rendered functionally inactive by any suitable technique. For example, they may be rendered functionally inactive by deletions, substitutions or insertions, preferably by deletion. Deletions may remove portions of the genes or the entire gene. For example, deletion of only one nucleotide may be made, resulting in a frame shift. However, preferably larger deletions are made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Inserted sequences may include the heterologous genes described below. In particular, it is preferred to insert the heterologous gene into ICP27 or ICP4. In the case of the vmw65 gene, the entire gene is not deleted since it encodes an essential structural protein, but a small inactivating mutation is made which abolishes the ability of VMW65 to activate transcriptionally IE genes (e.g. as in Ace et al., 1989 or Smiley et al. 1997).

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences: The mutated sequence may comprise deletions, insertions or substitutions, all of which may be constructed by routine techniques. Insertions may include selectable marker genes, for example lacz or GFP, for screening recombinant viruses by, for example, b-galactosidase activity or fluorescence.

Heterologous Genes and Promoters

The viruses for use in the invention are typically modified to carry a heterologous gene. The term "heterologous gene" encompasses any gene. A heterologous gene may be a test gene for use in a method of target validation or a gene of therapeutic use for use in a method of treatment or in the manufacture of a medicament. Although a heterologous gene is typically a gene not present in the genome of a herpes virus, herpes gene/genes may be used provided that the coding sequence is not operably linked to the viral control sequences with which it is naturally associated.

The heterologous gene may be any allelic variant of a wild-type gene, or it may be a mutant gene. The term "gene" is intended to cover nucleic acid sequences which are capable of being at least transcribed. Thus, sequences encoding mRNA, tRNA and rRNA are included within this definition. However, the present invention is concerned with the expression of polypeptides or antisense RNA rather than tRNA and rRNA. The term "gene" covers a polynucleotide comprising the coding sequence of a polypeptide. The polynucleotide may include one or more introns, for example may comprise genomic DNA. Preferably the polynucleotide comprises cDNA. Sequences encoding MRNA or antisense RNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

A heterologous gene may be inserted into the viral genome by homologous recombination of HSV strains with, for example, plasmid vectors carrying the heterologous gene flanked by HSV sequences. The heterologous gene may be introduced into a suitable plasmid vector comprising herpes viral sequences using cloning techniques well-known in the art. The heterologous gene may be inserted into the viral genome at any location provided that the virus can still be propagated. It is preferred that the heterologous gene is inserted into an essential gene. Heterologous genes may be inserted at multiple sites within the virus genome.

The transcribed sequence of a heterologous gene is preferably operably linked to a control sequence permitting expression of the heterologous gene in a mammalian cell, preferably a cell of the peripheral nervous system. The term "operably linked" refers to a juxtaposition wherein the components described are in a relationship permitting them to function in their intended marmer. A control sequence "operably linked" to a coding sequence is ligated in such a way that expression of the coding sequence is achieved under conditions compatible with the control sequence.

The heterologous gene is under the control of a promoter active during herpes virus latency. Such promoters typically comprise fragments of the latency associated transcript (LAT) region of the virus or are chimaeric promoters comprising fragments of the LAT region together with a non-LAT promoter. Such latently active promoters may drive the expression of endogenous gene or genes from within the LAT region of the virus, or when inserted at an ectopic, non-LAT site within the HSV genome.

The control sequence comprises a promoter allowing expression of the heterologous gene and a signal for termination of transcription. The promoter is selected from promoters which are functional during herpes latency in mammalian, preferably rat, mouse, guinea pig, ferret, primate or human, cells of the central nervous system. The promoter/promoters may be derived from promoter sequences of eukaryotic genes. For example, promoters may be derived from the genome of a cell in which expression of the heterologous gene is to occur, preferably a mammalian, preferably human cell of the peripheral nervous system. With respect to eukaryotic promoters, they may be promoters that function in a ubiquitous manner (such as promoters of β-actin, tubulin) or, alternatively, a tissue-specific manner, such as the neuron-specific enolase (NSE) promoter. They may also be promoters that respond to specific stimuli, for example promoters that bind steroid hormone receptors. Viral promoters may also be used, for example the Moloney murine leukemia virus long terminal repeat (MMLV LTR) promoter or other retroviral promoters, the human or mouse cytomegalovirus (CMV) IE promoter, or promoters of herpes virus gene including those driving expression of the latency associated transcripts.

Expression cassettes and other suitable constructs comprising a heterologous gene and control sequences can be made using routine cloning techniques known to persons skilled in the art (sec, for example, Sambrook et al., 1989, Molecular Cloning—A Laboratory Manual; Cold Spring Harbor Press).

It may also be advantageous for the promoters to be inducible so that the levels of expression of the heterologous gene can be regulated during the life-time of the cell. Inducible means that the levels of expression obtained using the promoter can be regulated. For example, in a preferred embodiment where more than one heterologous gene is inserted into the HSV genome, one promoter would comprise a promoter responsive to the tet repressor/VP 16 transcriptional activator fusion protein previously reported (Gossen and Bujard, 1992, Gossen et al., 1995), and driving the heterologous gene the expression of which is to be regulated. The second promoter would comprise a strong promoter (e.g. the CMV IE promoter) driving the expression of the tet repressor/VP 16 fusion protein. Thus in this example expression of the first heterologous gene would depend on the presence or absence of tetracycline.

In the current invention, a promoter, or more than one promoter, is used which allows gene expression during herpes virus latency. Such promoters may be derived from the LAT region (e.g. LAP2; Goins et al. 1994) and may be chimaeric promoters containing sequences from the LAT region fused to a non-LAT promoter or other clements (e.g. Lachmann and Efstathiou, 1997). These promoters may function from within the endogenous LAT region of the virus or when inserted at a heterologous site in the virus genome. In particularly preferred embodiments chimaeric promoters consisting of a non-LAT promoters such as the CMV, MMLV or NSE promoters, or fragments thereof, linked to LAT-derived sequences, including those present in LAP1 (Goins et al. 1994), LAP2 (Goins et al. 1994) and/or LAT. The LAT P2 region is here defined as HSV1 nucleotides 118866–120219 of HSV strain 17+(GenBank HE1CG: from PstI-BstXI sites), and includes fragments or derivatives of this region, including homologous regions of other HSV1 strains and of HSV2 strains, which are capable of providing a long-term expression capability to promoters to which they are linked. Such chimaeric promoters may also allow the expression of multiple heterologous genes by placing pairs of promoters away from a central LAT-derived element such that two genes may be expressed from a single expression cassette (e.g. as in Thomas et al. 1999).

Heterologous genes in viruses for therapeutic uses will typically encode polypeptides of therapeutic use. For example, genes which may prevent further degeneration of the cells affected in a particular disease, stimulate new cells to be produced, or affect the metabolic functioning (e.g. by the delivery of genes encoding enzymes) of the cell. Combinations of such factors might also be delivered using a single vector virus. Heterologous genes may be wild-type genes or may be mutated to enhance the function of the gene or to inhibit function of the gene. For example, where an endogenous gene is over expressed in a central nervous system disorder, a non-functional gene which disrupts the function of the endogenous gene may be useful in treating the disorder.

In particular, the heterologous gene/genes may encode a polypeptide capable of preventing, reducing or reversing cellular degeneration in degenerative diseases such as Parkinson's disease or Alzheimer's disease, or in increasing the activity of the remaining cells in such diseases. Such genes include neurotrophic factors such as GDNF and related proteins, or enzymes such as tyrosine hydroxylase or GTP-cyclohydrolase each of which may be of benefit in the treatment of Parkinson's disease, or genes encoding proteins such as Sonic Hedgehog or Nurr-1. Other examples of potentially beneficial genes include those which are deficient in metabolic diseases such as Tay-Sachs or mucopolysacharide diseases or other diseases for which a genetic defect is known.

Suitable heterologous genes include growth factors such as NT-3, Rega-2, CNTF, GDNF, BDNF and NGF and factors of unknown function. The present invention may be used to attempt to identify the function of such factors, for example by determining the effect of the factor of unknown function on a cell of the central nervous system. Genes encoding factors of unknown function may typically have been implicated in a central nervous system disorder.

Heterologous genes may also include marker genes (for example encoding β-galactosidase or green fluorescent protein or other fluorescent proteins) or genes whose products regulate the expression of other genes (for example, transcriptional regulatory factors including the tet repressor/vmw65 transcriptional activator fusion protein described above).

Target validation, gene therapy, and other therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus multiple heterologous genes can be accommodated within its genome. There are, for example, at least two ways in which this could be achieved. For example, more than one heterologous gene and associated control sequences could be introduced into a particular HSV strain either at a single site or at multiple sites in the virus genome. It would also be possible to use pairs of promoters (the same or different promoters) facing in opposite orientations away from each other, these promoters each driving the expression of a heterologous gene (the same or different heterologous gene) as described above.

A virus may comprise one, two, three, four or more heterologous genes. Where the gene is a test gene for use in a method of target validation, the virus typically comprises one heterologous gene. The virus may comprise one, two or more copies of a heterologous gene. A virus for use in a method of target validation may comprise more than one heterologous test gene. This will enable several genes, for example from 2 to 20 genes, preferably from 2 to 10 genes, for example, 4, 6 or 8 genes, to be screened simultaneously. If an effect of a test gene is observed, further viruses carrying fewer test genes, for example one or two test genes, may be used to determine which of the genes is responsible for the observed effect.

Heterologous genes for use in target validation methods will typically be implicated in a central nervous system disorder. For example, a gene may be implicated in a disorder due to its presence on region of a chromosome linked to the disorder. Alternatively a gene may be implicated in a central nervous system disorder if it is known to be expressed in the central nervous system. A gene implicated in a central nervous system disorder may be upregulated or down-regulated in a tissue in a natural, artificial or inducede disease state. Other suitable test genes include genes that encode proteins which are involved in nerve cell growth and/or regeneration such as neuronal growth factors.

Monitoring Phenotype

As used herein the term "phenotype" is used to refer to any physical manifestation of a disorder of the central nervous system. The term "phenotype" is thus intended to include changes at the molecular, cellular, tissue, cognitive and behavioural levels. Damage and trauma to the central nervous system, for example as a result of physical and chemical injury is also included within the term "phenotype".

Any suitable phenotype associated with a central nervous system disorder may be monitored. For example, the motor control of an animal may be monitored using any suitable assay for monitoring the motor activity or behavior of an animal in response to a suitable stimulus. The test animal may be a rodent, primate or other laboratory animal. A test gene which influences the phenotype will typically enhance or diminish the response of the animal to a given stimulus. Control responses may be determined by testing an animal prior to inoculation with the virus or by testing one or more control animals. A control animal is an animal which has not been inoculated with a virus or which has been inoculated with a control virus which does not express a heterologous gene or which expresses a heterologous gene that does not affect the phenotype of interest. Cognitive function of an animal may also be monitored. Assays for monitoring motor activity and cognitive function are known in the art.

A phenotype associated with a central nervous system disorder may also be monitored at the cellular or molecular level. This is particularly important when monitoring the effect of a test gene in vitro. For example, the cellular response to the application of a chemical stimulus such a neurotransmitter or agonist or antagonist of a neurotransmitter receptor may be monitored. This may be achieved using electrophysiological techniques. Alternatively any changes in gene expression within a central nervous system cell in response to the test gene may be monitored.

A phenotype may be the susceptibility of an animal to a disease. A method of the invention may therefore be a method of determining the role of a gene in the susceptibility of an animal to a nervous system disorder. For example, following inoculation of a test animal with a test gene, a factor associated with a nervous system disorder may be administered to the animal, or the animal may be exposed to such a factor, and the onset of symptoms of the disorder may be monitored and compared to the onset of symptoms in a control animal. Typically, a factor associated with a nervous system disorder is thought to be a causative factor in the onset of the disorder. Alternatively, onset or development of a disease may be monito red over time in the absence of a specific factor. For example, a test gene may promote or delay the onset of a neurological disorder.

A test gene may be suitable as a target for gene therapy or for small molecule modulators useful in the treatment of a central nervous system disorder if it influences a phenotype associated with the disorder. A gene identified as a target using a method of the invention may be used in a method of screening for agents useful in the treatment of a central nervous system disorder if it influences a phenotype associated with the disorder. Generally a test gene may be considered to influence a phenotype if it inhibits or enhances the phenotype, for example expression of a phenotype may be increased or decreased by at least 5%, for example by at least 10%, at least 15%, at least 20% or at least 25%, preferably by at least 30%, for example at least 40% or at least 50%, more preferably by at least 70%, for example, at least 80% or at least 90% compared to controls.

Introducing Virus

A replication incompetent herpes virus as described herein may be introduced into the central nervous system by any suitable means. For example, by injection into the brain, spinal cord or ventricles within the brain. A replication incompetent herpes virus as described herein is preferably introduced into one or more sites within the brain, for example into the striatum, spinal cord, cortex, cerebellum, hippocampus or brain stem. The expression of a heterologous reporter gene in the virus may be monitored at the site of delivery and at remote sites within the central nervous system to determine the efficiency of gene expression. Preferably, the heterologous gene is expressed at the site of delivery and at least one connected site.

Therapeutic Uses

Viruses of the invention may be used in methods of therapy in the treatment of nervous system disorders. As used herein, the term "disorder" is intended to include any condition of the nervous system which affects the normal functioning of the nervous system. "Conditions", "diseases" and "injury" to the central nervous system are thus encompassed by the term "disorder". The term "disorder" also includes animal models of peripheral nervous system disorders. In particular, viruses of the invention may be used for the treatment of neurodegenerative diseases such as Parkinson's disease, stroke or Alzheimers disease, or in single gene defect diseases such as mucopolysaccharide diseases or Tay-Sachs disease.

Replication incompetent herpes viruses capable of infecting cells of the central nervous system and expressing a heterologous gene at a site connected to but distinct from the site of infection as described herein may be used in methods of therapy. In particular, viruses of the invention may be used for the treatment of neurodegenerative diseases.

The herpes viruses of the present invention may thus be used to deliver therapeutic genes to a human or animal in need of treatment. Delivery of therapeutic genes using the herpes viruses of the invention may be used to treat central nervous system disorders, for example diseases such as Alzheimer's disease or Parkinson's disease, or to improve cognitive function, for example following stroke injury. Generally, the condition of a patient suffering from a central nervous system disorder is improved by administration of the virus. Administration of the herpes virus vector to a subject suffering from disorder of the central nervous system typically alleviates the symptoms of the disorder an/or prevents the progression of the disorder One method of administering therapy involves inserting a therapeutic gene into the genome of the herpes virus of the invention, as described above, and then combining the resultant recombinant virus, as active ingredient, with a pharmaceutically acceptable carrier or diluent to produce a pharmaceutical composition. Suitable carriers and diluents include isotonic saline solutions, for example phosphate-buffered saline.

Gene delivery to cells of the peripheral nervous system may be carried out by direct injection of the vector composition into a single site, or into two or more sites, of the central nervous system of a human or animal. The amount of virus administered is in the range of from $10^4$ to $10^{10}$ pfu, preferably from $10^5$ to $10^8$ pfu, more preferably about $10^6$ to $10^8$ pfu. When injected, typically from 1–200 µl preferably from 1 to 10 µl of virus suspension, depending on the species, in a pharmaceutically acceptable suitable carrier or diluent, is administered.

The routes of administration and dosages described are intended only as a guide since a skilled practitioner will be able to determine readily the optimum route of administration and dosage. The dose of a modulator may be determined according to various parameters, especially according to the substance used; the age, weight and condition of the patient to be treated; the route of administration; and the required regiment. A physician will be able to determine the required dosage for any particular patient.

The herpes viruses of the present invention may thus be used to deliver therapeutic genes to a human or animal in need of treatment. Delivery of therapeutic genes using the herpes viruses of the invention may be used to treat for example Parkinson's disease or Alzheimer's disease or other neurodegenerative conditions.

One method of administering therapy involves inserting the therapeutic gene/genes into the genome of the herpes virus of the invention, as described above, and then combining the resultant recombinant virus with a pharmaceutically acceptable carrier or diluent to produce a pharmaceutical composition. Suitable carriers and diluents include isotonic saline solutions, for example phosphatebuffered saline.

Gene delivery to cells of the nervous system may then be carried out following direct injection of the vector composition into a site or into two or more sites within the brain of a human or animal. The amount of virus administered is in the range of from $10^4$ to $10^4$ pfu, preferably from $10^5$ to $10^8$ pfu or $10^6$ to $10^8$ pfu, more preferably about $10^6$ to $10^7$ pfu. When injected, typically from 1 to 200 µl, preferably from 1 to 10 µl, of virus suspension in a pharmaceutically acceptable suitable carrier or diluent, depending on the species and site of inoculation, is administered.

The routes of administration and dosages described are intended only as a guide since a skilled practitioner will be able to determine readily the optimum route of administration and dosage for any particular patient depending on, for example, the age, weight and condition of the patient.

The invention will be described with reference to the following Examples, which are intended to be illustrative only and not limiting.

EXAMPLES

Materials and Methods

Construction and Growth of Viral Strains

Replication incompetent virus strains are derived from HSV1 strain 17+, the nucleotide sequence of which is deposited in GenBank (Accession No. HEICG). These can be propagated on 27/12/M:4 cells which are BHK cells containing the HSV ICP27 and ICP4-encoding genes and equine herpes virus gene 12 (Thomas et al., 1999). These cells allow efficient growth of viruses with mutations in ICP4, ICP27 and with mutations in vmw65 reducing its transactivating activity. Alternatively B 130/2 cells which complement mutations to only ICP27 (Howard et al. 1998) are used for the growth of viruses disabled by the mutation ICP27 alone. These cell lines only complement the genes which have been deleted and there is no sequence overlap between the viral and cellular genomes.

The pR20.5 and pR19 promoter cassettes are shown in FIG. 1. The pR20.5 cassette was inserted into a plasmid allowing insertional inactivation of UL41, the gene encoding vhs (insertion at the unique NruI site at the nucleotide 91854 in UL 41). The pR19lacZ and pR19GFP cassettes used here (see FIG. 1) were recombined into the endogenous LAT regions between the two BstXI sites (nt 120220 and 120408). HSV 1 nucleotide numbers refer to GenBank file HE1CG.

The current invention was exemplified using virus strain 1764/27-/4-/pR19lacZ. The term 1764 describes a virus with the in 1814 mutation in the gene encoding VMW65 and with the genes encoding ICP34.5 and ORF P completely deleted (between nucleotides nt 124945–125723). The term 27—refers to the deletion of nucleotides 113273–116869, which contain the genes UL54, 55 and 56. UL54 is the gene encoding the essential IE gene ICP27 and UL55 and 56 are both nonessential genes. Hence, 1764/27-/4-virus is deleted for ICP34.5, ICP27 and ICP4 with an inactivating mutation in vmw65 as previously described for virus strain 1764/27-/4-/PR20.5 (Thomas et al. 1999). This virus however contains a CMV promoter (from pcDNA3; Invitrogen)/lacZ (pCH I 10; Pharmacia)/poly A (from pcDNA3) cassette inserted into both copies of the LAT region between the BstXI sites at nts 120,219 and 120,413 rather than the insertion into ICP4 described in Thomas et al. 1999. Before insertion of the CMV/lacZ cassette in 1764/27-/4-/pR19lacZ the lacZ/GFP insertion into ICP4 in 1764/27-/4-/PR20.5 was removed by recombination with empty ICP4 flanking regions and selection of virus plaques which did not express lacZ or GFP giving virus strain 1764/27-/4-/w. The pR19lacZ cassette is capable of gene expression during HSV latency as described in WO 98/30707.

Virus strain 17+/pR19lacZ contains an identical insertion into the LAT region as in virus strain 1764/27-/4-/pR19lacZ, is disabled only by the deletion of ICP27, and has been described before (Wagstaff et al. 1998). Virus strain 1764/27-/4-/CMVlacZ/US5 contains a CMV/lacZ/polyA insertion into the unique SacI site in the non-essential US5 gene of 1764/27-/4-/w. The CMV promoter in such a context is not active during latency.

Virus strains 1764/27- and 1764/27-/4- were also deleted for the endogenous LAT P2 regions (between nucleotides 118768 and 120470, DdeI to HpaI) in order to prevent the recombinational instability which has otherwise been found to occur following insertion of LAT P2 containing expression cassettes outside of the LAT region.

The viral vector backbones used in the Examples are summarised in FIG. 1a and the promoter cassettes used in the Examples are shown in FIG. 1b.

Example 1
Replication Incompetent HSV Vectors Containing a Long-term Promoter and Deleted for ICP27 do not Allow Widespread Gene Delivery in the Brain Following Inoculation at a Single Site.

5 µl of virus strain 17+/pR19lacZ at a titre of 1×10$^8$ pfu/ml was inoculated into the striatum of 200–220 g female Lewis rats using stereotaxic procedures and a glass micropipette for inoculation. Virus suspension was administered at a rate of 0.5 µl/min. Pairs of animals were perfusion fixed at either 3 days, 1 week or 1 month post-inoculation, and sectioned and stained with X-gal as previously described (Howard et al. 1998). Brain sections showed robust X-gal staining in the striatum at 3 days post-inoculation which had reduced to some extent by 1 week and which was evident in only small numbers of cells by 1 month. However there was no significant X-gal staining evident at sites in the brain connected to the striatum such as the substantia nigra, from which dopaminergic neurons project, at any of the time points tested. Therefore using a replication incompetent virus backbone which still allows significant immediate early gene expression (ICP27 deleted; Thomas et al. 1999) and a promoter which does otherwise allow gene expression during herpes latency gene delivery is only observed at the inoculated site within the brain and not also at connected sites such as the substantia nigra (other than a small number of cells) where significant gene expression might have been expected had efficient retrograde transport followed by gene expression occurred.

Example 2
Replication Incompetent HSV Vectors Vectors Containing a Short-term Promoter, Deleted for ICP27 and ICP4 and with an Inactivating Mutation in vmw65, do not Allow Widespread Gene Delivery in the Brain Following Inoculation at a Single Site.

5 µl of virus strain 1764/27-/4-/CMVlacZ/US5 at a titre of 1×10$^8$ pfu/ml was inoculated into the striatum of 200–220 g female Lewis rats using stereotaxic procedures as in Example 1. Pairs of animals were again perfusion fixed at either 3 days, 1 week or 1 month post-inoculation, and sectioned and stained with X-gal. Brain sections again showed robust X-gal staining in the striatum at 3 days post-inoculation which had reduced by 1 week and but which in this case was undetectable by 1 month post-inoculation. There was no X-gal staining evident at sites in the brain connected to the striatum at any of the time points tested. Therefore using a replication incompetent virus backbone in which immediate early gene expression has been minimised (ICP4 and ICP27 deleted, vmw65 mutation reducing transactivation; Thomas et al. 1999) and a promoter which does not allow gene expression during herpes latency, gene delivery is again only observed at the inoculated site within the brain and not also at connected sites such as the substantia nigra where gene expression might have been expected had retrograde transport followed by gene expression occurred.

Example 3
Replication Incompetent HSV Vectors Vectors Containing a Long-term Promoter, Deleted for ICP27 and ICP4 and with an Inactivating Mutation in vmw65 Allow Gene Delivery to Multiple Sites in the Brain Following Inoculation to only a Single Site.

Injections into the rat striatum, spinal cord or superior colliculus were carried out with the 1764/27-/4-/pR19lacZ. 5 µl of virus strain 1764/27-/4-/pR19lacZ at a titre of 1×10$^8$pfu/ml was inoculated into the striatum of 200–220 g female Lewis rats as above and brains removed and sectioned at time points as before. Brain sections again showed high efficiency gene delivery in the striatum at 3 days post-inoculation with large numbers of X-gal staining cells also evident at 1 week and 1 month after inoculation. However, unlike in the previous Examples, significant X-gal staining was observed in the substantia nigra. Therefore using both a replication incompetent virus backbone in which IE gene expression has been minimised and a promoter active during virus latency, gene delivery is observed at both the inoculated site within the brain, in this case the striatum, and also at connected sites such as in this case the substantia nigra. This results from highly efficient retrograde transport following inoculation in the striatum allowing gene expression in neuronal cell bodies in the substantia nigra from which they project.

Adult Lewis rats were also stereotaxically injected with 2.5×10$^5$ pfu of 1764/27-/4-/pR19lacZ at the C6 level of the spinal cord or into the superior colliculus and thalamus. Three weeks after injection, the animals were perfusion fixed and relevant areas of the nervous system were sectioned and stained for lacZ expression.

In each case, the virus gave high level gene expression at the site of injection and was also efficiently transported from the site of injection to the cell bodies at connected sites where gene expression occured. This was clearly demonstrated by the transport of the disabled virus from the striatum to the substantia nigra, from the superior colliculus via the optic nerve to the retinal ganglion cells, and from the C6 level of the spinal cord to DRGs, the brainstem and areas of the hind and midbrain

Example 4

Virus Strain 1764/27-/4- does not Express Significant Amounts of any Immediate Early Gene.

To test the levels of residual IE gene expression of a virus deleted for ICP27 and/or ICP4 and with VMW65 inactivated, non-complementing BHK cells were infected at MOIs of 10, 5 and 1 with 17+27-, 1764 27- and 1764 27-4-viruses. Complementing 27/12/M:4 cells were infected with the same viruses at an MOI of 1 as positive control. Cells were harvested 48 hours post infection and analyzed for the expression of ICP0, ICP22 and ICP47 by western blotting. Samples for western blot analysis were prepared by standard techniques. Extract from approximately $10^5$ cells was loaded per lane of an SDS-polyacrylamide gel. Proteins were transferred to nitrocellulose and probed with appropriate antibodies by standard techniques. Antibody against HSV 1 ICP0 was purchased from ABI. Antibodies to HSV1 ICP22, ICP6 and ICP47 were provided by Bernard Roizman, Barkie Clements and David Johnson respectively. Detection was performed using ECL chemiluminescence (Amersham).

The 17+27-virus expressed significant amounts of all three of the IE genes which have not been deleted (ICP0, ICP22 and ICP47). The subsequent inactivation of VMW65 and deletion of ICP34.5 (the 1764 27-virus) leads to reduced but still significant levels of ICP0, ICP22 and ICP47 expression. This suggests that the inactivating mutation in VMW65 in the context of an ICP27 deleted virus is not sufficient to completely prevent the transactivation of the remaining IE gene promoters. However, prevention of transactivation of the other IE gene promoters can be achieved by the additional deletion of ICP4 (the 1764 27-4-virus). The western blots for ICP0, ICP22 and ICP47 reveal that there is no detectable expression of any of these IE genes from this virus, even at high multiplicity of infection.

The 1764 27-4-virus does not therefore express significant amounts of any of the IE genes. The essential IE genes ICP4 and ICP27 have been completely deleted from the viral backbone and the remaining IE genes ICP0, ICP22 and ICP47 are not expressed. This lack of IE gene expression requires the combination of VMW65 inactivation and ICP4/ICP27 deletion and provides a level of disablement to the virus similar to that resulting from the individual deletion of each of the IE genes (Samaniego et al., 1998).

Example 5

Virus Strain 1764/27-/4-pR20.5 Simultaneously Expresses High Levels of Two Exogenous Genes It has been previously reported that in the absence of IE gene products, the expression of inserted genes is undetectable in the majority of transduced cells even at short times post infection (Saminego et al. 1998). It has been proposed that this absence of transgene expression is attributable to an active repression of both HSV and non-HSV promoters by a cellular factor, but that this effect is masked in less disabled viruses by the presence of the potent viral transactivators VMW65, ICP0 and ICP4 (Preston and Nicholl 1997). Non-complementing BHK cells were infected at an MOI of 10 and visualized by fluorescence microscopy or processed to detect lacZ expression 48 hours post infection. Abundant transgene expression from the 1764/27-/4-pR20.5 virus was observed 48 hours post infection even though IE expression levels were minimal.

Example 6

Exogenous Gene expression from Cassettes Inserted into Virus Strain 1764/27-/4- is Dose Dependent in Non-complementing Cells.

The expression level of ICP22 and ICP47 from the 1764/27-virus in non-complementing cells was not dose dependent, the peak of expression occurring at an MOI of 1. This suggests that with this intermediately disabled virus, interactions between the virus genome and remaining viral factors are affecting virus gene expression. In order to examine this further, non-complementing BHK cells were infected with a selection of disabled viruses over a wider range of MOIs and the samples harvested 48 hours post infection. Western blots were then probed for the expression of ICP22 and ICP47 as before. This experiment showed that in the case of the 17+/27-virus, ICP22/47 expression is dose dependent, but with the 1764/27-virus, the peak of ICP22/47 expression is at an MOI of 0.5. No expression of ICP22 was detected at any MOI from the 1764/27-/4-virus. This phenomenon was investigated further and found to also apply to exogenous genes, for example CMV driven GFP, inserted into the 1764/27-virus but not the less disabled 17+/27-virus or the more disabled 1764/27-/4-virus. Virus strains 1764/27-/4-pR19GFP and 1764/27-/4-pR20.5 demonstrate a dose dependent pattern of GFP expression. However, with virus strain 1764/27-/pR20.5 the pattern of GFP expression follows that of ICP22/47, with expression levels peaking at an MOI of 0.5. The reason for this expression pattern is unclear, but a similar dose effect has been reported previously when ICP0 and ICP4 were used in combination to activate IE gene target promoters in transient transfection assays (Gelman and Silverstein 1987). Whatever the mechanism, a linearly dose dependent pattern of transgene depression such as is directed by the most disabled virus is more desirable in gene delivery applications than the pattern shown by the less disabled virus.

Example 7

Virus Strain 1764/27-4-Directs High Efficiency Gene Delivery to Cultured Neurons.

In order to test the ability of 1764 27-4-viruses to deliver exogenous genes to cultured neurons, primary cultures of DRG neurons were infected at an MOI of 10 with 1764/27-/4-/pR20.5. Mock infected neurons or neurons infected with virus strain 17+/27-/pR 19GFP were used as controls. One week post infection, neurons were photographed under phase contrast and fluorescence microscopy. Both viruses were able to efficiently deliver exogenous genes to neurons in culture. However, by 7 days post infection, the 17+/27-virus caused considerable toxic effects, with loss of supporting cells, clumping of neuronal cell bodies and retraction of neuronal processes. In contrast, cells infected the 1764/27-4-virus are indistinguishable in morphology from mock infected cells under phase contrast microscopy. Neurons infected with the 1764/27-/4-virus express abundant levels of GFP, in both neuronal cell bodies and processes, demonstrating efficient gene delivery.

Example 8
Virus Strain 1764/27-4-Directs the Expression of Delivered Genes for Extended Periods in Neuronal and Non-neuronal Cells.

In order to test whether the 1764/27-/4-virus could establish a persistent infection, Vero cells at 50% confluence were infected at an MOI of 10 with virus strain 1764/27-/4-/pR20.5. Following infection, cells were maintained in 2% serum at 34° C., and reporter gene expression was monitored at 3, 7 and 23 days post infection. At the last time point (23 days), a duplicate well was superinfected at an MOI of 5 with virus strain 17+/27-(expressing no reporter gene). GFP expression was evident at all time points during the experiment, and that unlike in the previously published work (Samaniego et al 1998), superinfection is not necessary for transgene expression to occur. GFP expression is present in reducing numbers of cells over time, as in previous work, which is probably due to cell division in the culture and the finite life span of both transduced and untransduced cells. Superinfection of the cultures at 23 days does increase GFP expression levels slightly but the effect is not marked. This demonstrates that the genome of virus strain 1764/27-/4-/pR20.5 is capable of persisting in the nucleus of infected cells, indicating the low toxicity of the vector. At all times up to the end of the experiment, the cells infected with virus strain 1764/27-/4-/pR20.5 were indistinguishable from mock infected cells.

In order to extend these findings, the expression characteristics of virus strain 1764/27-/4-/pR20.5 in rat organotypic hippocampal slice cultures was also investigated. Organotypic hippocampal slice cultures were prepared and infected 7 days later with $1\times10^6$ pfu of 1764/27-/4-/pR20.5. Infected slices were stained for lacZ together with expression of GFP at 2 days, 7 days and 21 days after infection.

A high level of transgene expression was observed at 2 days post infection, was maintained at 1 week and was still clearly detectable in the cultures 3 weeks after infection, albeit in a reduced number of cells. The processes of transduced neurons, even at the 3 week time point, were not swollen or beaded suggesting that degeneration of transduced neurons had not occurred. Infected cultures maintained normal morphology and did not differ from mock-infected control cultures at any time. These results again suggest that the toxic effects of 1764 27-4-pR20.5 on transduced cells are minimal, at least by morphological criteria, even over extended periods in culture.

References

Fink et al. 1996 Ann Rev Neurosci 19;265–287
Goldstein and Weller 1988 J Virol 62;196–205
Ho and Mokarski 1988 Virology 167;279–283
Lokensgard et al. 1994 J. Virol 68;7148–7158.
Dobson et al. 1990 J. Virol. 69;2264–2270
Goins et al. 1994 J. Virol 68;2239–2252.
Lachmann and Efstathiou 1997 J. Virol 71;3197–3207
Samaniego et al. 1998 J. Virol 72;3307–3320
Krisky et al. 1998 Gene Therapy 5;1593–1603
Thomas et al. 1999 J. Virol 73;7399–7409
Howard et al. 1998 Gene Therapy 5;1137–1147
Wagstaff et al. 1998 Gene Therapy 5;1566–1570
Samaniego LA et al. J. Virol. (1995); 69:5705–5715
Coffin RS and Latchman DS (1996). In: Genetic Manipulation of the Nervous
System (DS Latchman Ed.) pp 99–114: Academic Press, London.
Coffin RS, et al. (1996) Gene Therapy, 3, 886–891.
Ace CI, et al. (1989) J. Virol., 63,2260–2269.
Smith, IL et al., 1992, Virology 186:74–86.
Rice, SA and Knipe DM., 1990, J. Virol 64:1704–1715.
DeLuca NA et al. J. Virol. 1985; 56: 558–570.
MacFarlane M, et al. (1992) J. Gen. Virol., 73,285–292.
Lokensgard JR, et al. (1994) J. Virol., 68,7148–7158.
Gossen M and Bujard H, 1992, PNAS 89:5547–5551.
Gossen M et al., 1995, Science 268:1766–1769.
Smiley, J. R., and J. Duncan. 1997. J. Virol. 71:6191–6193.
Johnson et al. 1994. J. Virol 68;6347–6362.
Johnson et al. 1992. J. Virol; 2952–2965
Wu et al. 1996. J. Virol 70;6358–6369
Sacks and Shaffer 1987 J Virol; 829–839
Stow and Stow 1986 J Gen Vir 67;2571–2585
Post and Roizman 1981 Cell 25;227–232
Sears et al. 1985 J. Virol 55;338–346
Deluca and Schaffer 1987 NAR 15;4491–4511
Samaniego et al. 1995 J. Virol 69;5705–5715
Samaniego etal. 1997 J. Virol 71;4614–4625
Batterson and Roizrnan 1983 J Virol 46;371–377
Pellet et al. 1985 PNAS 82;5870–5874
Bloom et al. 1995 Mol Br Res 3 1; 48–60
Carpenter and Stevens 1996 Hum Gen Ther 7; 1447–1454
Lokensgard et al. 1997 J. Virol 71;6714–6719
Preston and Nicholl 1997 J Viol 71;7807–7813
Gelmen and Silverstein 1987 J Virol 61;2286–2296 and 3167–3172
Sze and Hermen 1992 Virus Res. 26;141–152
Thompson et al. 1998 Virus Genes 1(3); 275–286
Meignier et al. 1988 J. Infect. Dis. 159;602–614

What is claimed is:

1. A method of determining whether a gene has an effect on a phenotype associated with a central nervous system disorder, which method comprises:
    (i) inoculating into a cell of the central nervous system a replication incompetent herpes virus comprising:
        (a) a mutation which prevents or reduces to minimal levels the expression of ICP27, ICP4, ICP22 and ICP0; and
        (b) a heterologous gene operably linked to a promoter active during herpes virus latency; and
    (ii) monitoring a phenotype of said disorder to determine whether expression of said heterologous gene in said cell changes said phenotype, thereby determining whether said heterologous gene has an effect on said phenotype,
wherein said cell is in vitro or is a non-human animal cell in vivo.

2. A method according to claim 1, wherein said cell is a non-human animal cell inoculated in vivo.

3. A method according to claim 1, wherein said virus lacks a functional gene encoding ICP4 and a functional gene encoding ICP27 and which has an inactivating mutation in the gene encoding vmw65 abolishing its transcriptional-activation activity.

4. A method according to claim 1, wherein said virus lacks functional genes encoding ICP27, ICP4, ICP0 and ICP22.

5. A method according to claim 1, wherein said virus is a herpes simplex virus 1.

6. A method according to claim 1, wherein said virus is a herpes simplex virus 2.

7. A method according to claim 1, wherein said promoter is a chimeric promoter containing elements of a latency associated transcript (LAT) region of a herpes virus and a non-LAT promoter.

8. A method according to claim 1, wherein said promoter is or contains elements from the LAP2 HSV promoter.

9. A method according to claim 1, wherein said promoter contains non-HSV elements such as an internal ribosome entry site (IRES) sequence or other sequence which performs a similar function.

10. A method according to claim 1, wherein said heterologous gene encodes a therapeutic polypeptide.

11. A method according to claim 10, wherein said polypeptide prevents or slows neuronal degeneration, reverses neuronal degeneration or stimulates cells remaining in the central nervous system of a subject suffering from a neurodegenerative disorder to perform a function of cells absent in said subject.

12. A method according to claim 1, wherein said heterologous gene is selected from the group consisting of a gene encoding a neurotrophic factor, a gene encoding an enzyme, a gene encoding Sonic Hedgehog or Nurr-1, and a gene deficient in a metabolic disease.

13. A method according to claim 1, wherein said heterologous gene is implicated in a central nervous system disorder.

14. A method according to claim 1, wherein said disorder is a neurodegenerative disorder.

15. A method according to claim 1, wherein said disorder is selected from the group consisting of stroke, Parkinson's disease, Alzheimer's disease, Tay Sachs disease and a mucopolysaccharide disease.

16. A method according to claim 1, wherein said cell is a mammalian cell.

17. A method according to claim 1, wherein said cell is a neuron.

18. A method according to claim 1, wherein said cell is in a non-human animal which models said disorder.

19. A method according to claim 18, wherein said animal is a transgenic animal.

20. A method according to claim 1, wherein said phenotype is selected from the group consisting of a motor control disorder and a cognitive deficit.

21. A method according to claim 1, wherein said heterologous gene is expressed in said cell following retrograde transport along axonal processes from the site of contact between said cell and said virus.

22. A method according to claim 1, wherein said heterologous gene is expressed at the site of contact between said cell and said virus and at least one other site in the central nervous system which site is distinct from the site of contact.

23. A method according to claim 2, wherein said cell is inoculated by injecting said virus into brain of a non-human animal subject.

24. A method according to claim 23, said injection is into striatum or ventricles within said brain.

25. A method according to claim 1, wherein expression of said heterologous gene enhances said phenotype.

26. A method according to claim 2, wherein in step (ii) said monitoring is Gamed out in vitro.

27. A method according to claim 26, wherein in step (ii) said phenotype is monitored at a molecular, cellular or tissue level.

28. A method according to claim 2, wherein in step (ii) said phenotype is monitored at a behavioral or cognitive level.

29. A method according to claim 2, wherein said phenotype is susceptibility of a non-human animal subject to said central nervous system disorder and expression of said heterologous gene in said cell promotes onset of symptoms of said disorder in said subject.

30. A method according to claim 2, wherein said phenotype is susceptibility of a non-human animal subject to said central nervous system disorder and expression of said heterologous gene in said cell delays onset of symptoms of said disorder in said subject.

31. A method according to claim 1, wherein said cell is inoculated in vitro.

32. A method according to claim 31, wherein in step (ii) said phenotype is monitored at a molecular or cellular level.

33. A method according to claim 32, wherein in step (ii) said change in phenotype is a change in gene expression in response to expression of said heterologous gene.

34. A method according to claim 32, wherein in step (ii) a cellular response to application of a chemical stimulus is monitored.

35. A method according to claim 34, wherein said chemical stimulus is selected from the group consisting of a neurotransmitter, an agonist of a neurotransmitter receptor and an antagonist of a neurotransmitter receptor.

36. A method according to claim 1, wherein said change in phenotype is a change compared to said phenotype in a control subject.

* * * * *